(12) United States Patent
Pfaendler

(10) Patent No.: US 8,415,339 B2
(45) Date of Patent: Apr. 9, 2013

(54) BACTERICIDAL ANTI-MRSA ACTIVE PHARMACEUTICAL COMPOSITION CONTAINING CARBAPENEMS

(76) Inventor: Hans Rudolf Pfaendler, Stockdorf (DE)

( * ) Notice: Subject to any disclaimer, the term of this patent is extended or adjusted under 35 U.S.C. 154(b) by 0 days.

(21) Appl. No.: 12/601,259

(22) PCT Filed: May 14, 2008

(86) PCT No.: PCT/EP2008/003896
§ 371 (c)(1),
(2), (4) Date: Nov. 21, 2009

(87) PCT Pub. No.: WO2008/141764
PCT Pub. Date: Nov. 27, 2008

(65) Prior Publication Data
US 2010/0173887 A1 Jul. 8, 2010

(30) Foreign Application Priority Data
May 21, 2007 (EP) .................. 07010068

(51) Int. Cl.
*A61K 31/43* (2006.01)
*A61K 31/407* (2006.01)
*A61K 31/397* (2006.01)
*A61K 31/00* (2006.01)

(52) U.S. Cl. ........... 514/197; 514/210.1; 514/210.11; 514/210.12; 514/210.13; 514/210.14

(58) Field of Classification Search ............ 514/197, 514/210.1–210.14
See application file for complete search history.

(56) References Cited

U.S. PATENT DOCUMENTS
4,426,377 A * 1/1984 Howarth ............ 424/114

FOREIGN PATENT DOCUMENTS
EP 0 041 768 12/1981
EP 0 120 613 10/1984
EP 0 384 410 8/1990

OTHER PUBLICATIONS

Database Medline [Online] US National Library of Medicine (NLM), Bethesda, MD, US; Oct. 1990, Saionji et al., "Antibacterial activity of imipenem in combination with ampicillin against methicillin-resistant strains of *Staphylococcus aureus*", XP002459413, Database accession No. NLM2086811 (abstract).
Sumita et al., "In Vitro Synergistic Activity between Meropenem and Other Beta-Lactams against Methicillin-Resistant *Staphylococcus aureus*", Eur. J. Clin. Microbial. Infect. Dis., vol. 10, No. 2 pp. 77-84 (1991).
Saionji et al., "Antibacterial Activity of Imipenem in Combination with Ampicillin Against Methicillin-Resistant Strains of *Staphylococcus aureus*", The Japanese Journal of Antibiotics, 43(10):1685-1697 (1990) (with English Abstract).
International Search Report and Written Opinion dated Oct. 2, 2008, in corresponding PCT Application No. PCT/EP2008/003896.

* cited by examiner

*Primary Examiner* — Shengjun Wang
(74) *Attorney, Agent, or Firm* — Edwards Wildman Palmer LLP; Mark D. Russett

(57) ABSTRACT

Pharmaceutical compositions containing a carbapenem of the structural formula I

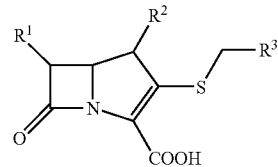

and epicillin are strongly bactericidal against MRSA and MRSE. Equivalently, compositions of conventional carbapenem antibiotics and epicillin are highly synergistic in eradicating said bacteria.

10 Claims, No Drawings

BACTERICIDAL ANTI-MRSA ACTIVE PHARMACEUTICAL COMPOSITION CONTAINING CARBAPENEMS

CROSS-REFERENCE TO RELATED APPLICATIONS

This application is the 35 U.S.C. §371 national stage of PCT application PCT/EP2008/003896, filed May 14, 2008, which claims priority to European Patent Application No. 07010068.0, filed May 21, 2007. The contents of these applications are incorporated herein by reference in their entirety.

DESCRIPTION AND BACKGROUND OF THE INVENTION

This invention relates to 2-S/O— and S/N formaldehyde acetal derivatives of carbapenem-3-carboxylic acids of the general formula I

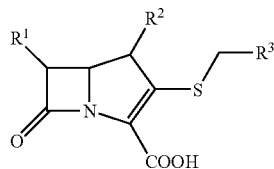

wherein $R^1$ denotes hydrogen, hydroxymethyl or 1-hydroxyethyl, $R^2$ denotes hydrogen or methyl and $R^3$ denotes a pharmaceutically acceptable group which is bonded to the remaining part of the molecule by an oxygen-carbon single bond or a nitrogen-carbon single bond and which is selected from the group comprising substituted or unsubstituted: alkoxy, alkenyloxy, alkinyloxy, cycloalkoxy, N-heterocyclyl, heterocyclyloxy, heterocyclylcarbonyloxy, heterocyclylthiocarbonyloxy, acyloxy, thioacyloxy, alkoxycarbonyloxy, carbamoyloxy, thiocarbamoyloxy, heterocyclyloxycarbonyloxy, heterocyclyloxythiocarbonyloxy, N-heterocyclycarbamoyloxy, N-heterocyclylthiocarbamoyloxy, heterocyclylcarbonylamino, heterocyclylthiocarbonylamino, heterocyclyloxycarbonylamino, acylamino, alkoxycarbonylamino, alkoxythiocarbonylamino, thioacyclamino, N-heterocyclylcarbamoylamino, N-heterocyclylthiocarbamoylamino, carbamoylamino, thiocarbamoylamino, imidoylamino, guanidino, N-heterocyclyl-alkoxycarbonylamino, N-heterocyclyl-alkylthiocarbonylamino and N-sulfonylamino where the foregoing alkyl, alkenyl, alkinyl, acyl, thioacyl or imidoyl molecule parts contain 1 to 6 carbon atoms and the heterocyclyl moiety is monocyclic or bicyclic and contains 3 to 10 ring atoms, of which one or more are selected from the series comprising: oxygen, sulphur and nitrogen and where the substituents of the above-mentioned groups R may be: alkyl, acyl, thioacyl, heterocyclyl, hydroxyl, hydroxyalkyl, alkoxy, hydroxyalkoxy, aminoalkoxy, amidinoalkoxy, guanidinoalkoxy, acyloxy, heterocyclyloxy, alkylheterocyclyloxy, hydroxyalkylheterocyclyloxy, aminoalkylheterocyclyloxy, carbamoyl, alkylcarbamoyl, dialkylcarbamoyl, carbamoyloxy, alkylcarbamoyloxy, dialkylcarbamoyloxy, thiocarbamoyl, alkylthiocarbamoyl, dialkylthiocarbamoyl, thiocarbamoyloxy, alkylthiocarbamoyloxy, dialkylthiocarbamoyloxy, mercapto, alkylthio, hydroxyalkylthio, aminoalkylthio, monoalkylaminoalkylthio, dialkylaminoalkylthio, amidinoalkylthio, acylthio, heterocyclylthio, alkylheterocyclylthio, hydroxyalkylheterocyclylthio, aminoalkylheterocyclylthio, carbamoylthio, monoalkylcarbamoylthio, dialkylcarbamoylthio, thiocarbamoylthio, alkylthiocarbamoylthio, dialkylcarbamoylthio, amino, monoalkylamino, hydroxyalkylamino, aminoalkylamino, dialkylamino, oxo, oximino, or alkylimino, imidoylamino, alkylimidoylamino, dialkylimidoylamino, tetraalkylammonium, cycloalkylamino, heterocyclylamino, alkylheterocyclylamino, heterocyclylcarbonylamino, alkylheterocyclylcarbonylamino, acylamino, amidino, monoalkylamidino, dialkylamidino, guanidino, alkylguanidino, dialkylguanidino, carbamoylamino, thiocarbamoylamino, alkylcarbamoylamino, thiocarbamoylamino, alkylthiocarbamoylamino, nitro, chloro, bromino, fluoro, iodo, azido, cyano, alkylsulphinyl, alkylsulphonyl, sulphonamido, sulphamoyloxy, alkylsulphamoyloxy, alkylsulphonyloxy or sulpho, sulphoxy, carboxamido, N-monoalkylcarboxamido, N,N-dialkylcarboxamido or carboxy, where the substituents, independently of one another, occur once or several times and their alkyl moiety contains 1 to 6 carbon atoms, and where the heterocyclic moiety is monocyclic or bicyclic and contains 3 to 10 ring atoms, of which one or more are selected from the series comprising: oxygen, sulphur and nitrogen, which compounds and their pharmaceutically acceptable salts, esters and amide derivatives are useful as antibiotics and as β-lactamase inhibitors.

Pharmaceutically acceptable groups $R^3$, which are bonded via an oxygen-carbon single bond or a nitrogen-carbon single bond are groups as are customary, for example, in the field of β-lactam antibiotics or β-lactamase inhibitors. Such groups are found, for example, in M. S. Sassiver, A. Lewis in "Advances in Applied Microbiology", Ed. D. Perlman, Academic Press N.Y. (1970) or in many patents, e.g. U.S. Pat. No. 5,096,899.

The term "pharmaceutically acceptable salt" as used herein and in the claims, includes non-toxic acid and base salts and the salts of zwitterionic species. Salts with a base include inorganic salts such as sodium, potassium, magnesium and calcium, or ammonium and salts with non-toxic amines such as trialkylamines, alkanolamines, arginine or cyclic amines such as piperazine, procaine and other amines, which have been used to form salts of carboxylic acids. Salts with an acid include inorganic acid salts such as hydrochloride, sulfate, phosphate and the like and organic acid salts such as acetate, maleate, citrate, succinate, ascorbate, lactate, fumarate, tartrate and oxalate and other organic salts with acids which have been used to form salts with amines.

The pharmaceutically acceptable esters and amide derivatives as used herein, serve as prodrugs by being hydrolyzed in the body to yield the antibiotic per se. They are preferably administered orally since hydrolysis occurs principally under the influence of the digestive enzymes. Parenteral administration may be used in some instances where hydrolysis occurs in the blood. Examples of pharmaceutically acceptable esters and amide derivatives include physiologically hydrolyzable esters and amides known and used in the penicillin and cephalosporin fields as, e.g. in Advances in Drug Res. 17, 197 (1988). Such esters and amide derivatives are prepared by conventional techniques known in the art.

The compounds according to the invention have several asymmetric centers and can thus exist in several stereochemical forms. The invention includes the mixture of isomers and the individual stereoisomers. The most preferred compounds of formula I have the 1R, 5S and 6S configuration of the substituted carbapenem nucleus and the 1'R or the 1'S configuration of the 6-(1-hydroxyethyl) side chain. Additionally, asymmetric carbon atoms can be included in the substituent $R^3$. The invention includes the compounds having the R and S configuration in the substituent $R^3$.

Moreover, the invention also relates to conventional carbapenem antibiotics, which are commercially available or investigated for clinical use. A comprehensive report about such carbapenem antibiotics is given in Heterocycles 54, 497, 2001.

This invention also relates to pharmaceutical compositions containing carbapenem antibiotics and their preparation. It relates also to methods of treatment where such compositions are used when an antibiotic effect is indicated.

The terminology for compounds of this class may either be based upon the root name "carbapenem" which employs a trivial and simple system of nomenclature (used in the general description). Alternatively, these compounds can also be described by the nomenclature according to the Chemical Abstract system (bicyclo-nomenclature), which is more appropriate to describe individual compounds of this family. Therefore the Chemical Abstract nomenclature is used within the Example Section.

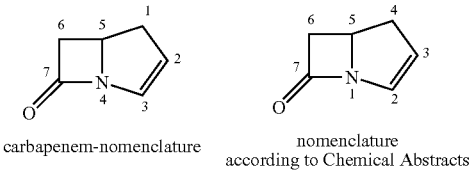 [SMILES: O=C1CC2CC=CN12 ; O=C1CC2CC=CN12]

carbapenem-nomenclature     nomenclature according to Chemical Abstracts

The classical β-lactam antibiotics such as the penicillins or the cephalosporins, have partly become ineffective in the therapy of infectious diseases because of bacterial resistance. Besides the natural resistance of certain bacteria, many strains of pathogenic microorganisms have acquired resistance with continuous use of antibiotics on a large scale. Thus, most species of *Staphylococcus aureus* have become resistant against the penicillins and many Gram-negative bacteria such as *Enterobacter cloacae, Pseudomonas aeruginosa* or even *Escherichia coli* have acquired resistance against the cephalosporins.

Although the carbapenems according to the invention are very active as mono-substances against penicillin sensitive *Staph. aureus* and penicillin resistant *Staph. aureus* that produce β-lactamase, they are not active against methicillin resistant *Staph. aureus* (MRSA) or methicillin resistant *Staph*. epidermis (MRSE). For example, four representative carbapenems exhibited only low activity against (methicillin resistant) *Staph*. Innsbruck with small inhibition zones of 0-12 mm in the plate test as described in U.S. Pat. No. 6,482, 818 or EP 1 100 800. The lack of activity against MRSA within the class of carbapenems is also documented, e.g. in EP 384 410. Resistance levels of MRSA have been increased considerably within the last decade and already in 2000 all marketed carbapenems completely lacked anti-MRSA activity (Journal of Antimicrobial Chemotherapy 2000, 45, 379).

Consequently, current research in the field of antibiotics is focused on methods to overcome growing MRSA and MRSE resistance, which might become a major threat to human life in near future.

*Staphylococcus aureus* is one of the most abundant bacterial pathogens in infectious diseases. In 2004, from diseases caused by *Staph. aureus*, 22.6% were reported resistant to methicillin or oxacillin (PEG-Resistenzstudie, Paul Ehrlich Gesellschaft für Chemotherapie e.V, www.p-e-g.org). The eradication of MRSA and MRSE is particularly difficult, because many species of these bacteria are also resistant to antibiotics that are not β-lactams, e.g. quinolone antibiotics.

MRSA resistance is not due to the formation of β-lactamase but to an entirely different mechanism, namely a lack of, or inadequate binding of the antibiotic to a penicillin binding protein PBP 2a, present with all MRSA strains. From this viewpoint, pharmaceutical preparations of penicillins or cephalosporins with β-lactamase inhibitors are not a solution to overcome resistance of MRSA and also the combination of amoxicillin and clavulanate is inappropriate in infections due to MRSA. (Journ. Antimicrob. Ther. 1989, 49.).

Another attempted method to overcome methicillin resistance was published in EP 384 410 with the description of a synergism between three carbapenems and penicillins or cephalosporins. The use of piperacillin and cefotiam in combination with imipenem was considered to be especially preferable in EP 384410. However, the above-mentioned combinations described by prior art are hardly sufficiently effective with reported mean MICs of 27.9 µg/ml for piperacillin/imipenem or 14.4 µg/ml for cefotiam/imipenem. Also a synergism between meropenem and cefpiramide (Eur. J. Clin. Microbiol. Infect. Dis. 10, 77-84, 1991) was reported with mean MICs of 13.2 µg/ml. Such high levels are impossible or very difficult to be maintained in vivo during the entire therapy. Although these combinations of prior art were more active than the individual components alone, a substantial improvement was desirable.

The fact that in EP 384410 was not validated in Germany, in the US and in other countries in 1995, indicates that the combinations described by prior art lack practicability.

As all marketed carbapenems currently used are administered parenterally because they do not have sufficient oral activity (Infection 14, (1986), suppl. 2, S 115) an orally active composition containing an (orally active) penicillin or a cephalosporin and a carbapenem could not be prepared by prior art. An orally active composition is desirable for the so called "switched therapy" in which the treatment is started with a parenteral formulation in the hospital and continued with the oral therapy after an earlier release of the patient. A more recent overview about oral carbapenems was given in Curr. Med. Chem.—Antiinfective Agents, 2000, 1, 1.

The current antibiotic of choice against MRSA infectious diseases is linezolide, a bacteriostatic agent (Chemotherapie Journal. 2002, 11, 113-6).

In order to overcome the resistance of MRSA we investigated the compositions of 29 conventional classical β-lactam antibiotics with 15 carbapenems for a possible synergism. For these investigations two highly resistant MRSA hospital strains, i.e. *Staph*. Innsbruck and MRSA 7268/02 were used. *Staph*. Innsbruck is resistant to oxacillin, methicillin, ampicillin and ciprofloxacin, MRSA 7268/02 is multiresistant to oxacillin, methicillin, enrofloxacin, clindamycin, ciprofloxacin and moxifloxacin. Such highly resistant bacteria have emerged recently and were not frequent 10 years ago.

Surprisingly we found, that from the investigated conventional β-lactam antibiotics (12 penicillins and 17 cephalosporins) epicillin showed an outstanding effect against MRSA of high resistance when combined with carbapenems. The synergistic effect of epicillin/imipenem was much higher than that of prior art using piperacillin/imipenem or cefotiam/imipenem. Time dependent counting of colony forming units (cfu) revealed that epicillin/imipenem at 2+2 µg/ml was also much faster in eradicating MRSA 7268/02 than other investigated penicillin/imipenem or cephalosporin/imipenem preparations described by prior art, including that of ampicillin/imipenem. With the epicillin/imipenem combination the number of cfu was decreased by 99.6% after 6 hrs of incubation at 37° C., revealing that this preparation is strongly bactericidal against MRSA 7268/02. In contrast, the especially preferred combinations described by prior art, namely piperacillin/imipenem or cefotiam/imipenem were only marginally bactericidal with reductions in cfu's by 17 or 71% respectively (Table 1)

TABLE 1

Bactericidal Effect of Combinations of Carbapenems and Penicillins or Cephalosporins against MRSA 7268/02

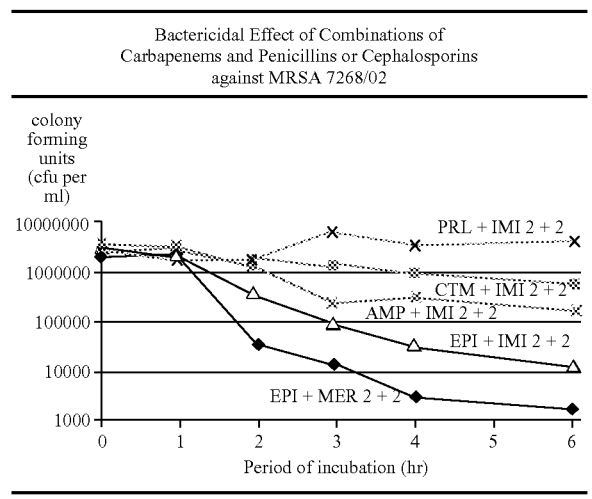

Neither epicillin, nor linezolide showed any significant reduction of cfu's, when used alone. Meropenem at 4 µg/ml was also less bactericidal than the epicillin/meropenem composition at 2+2 µg/ml (Table 2)

TABLE 2

Synergistic Effect of Epicillin and Meropenem against MRSA 7268/02

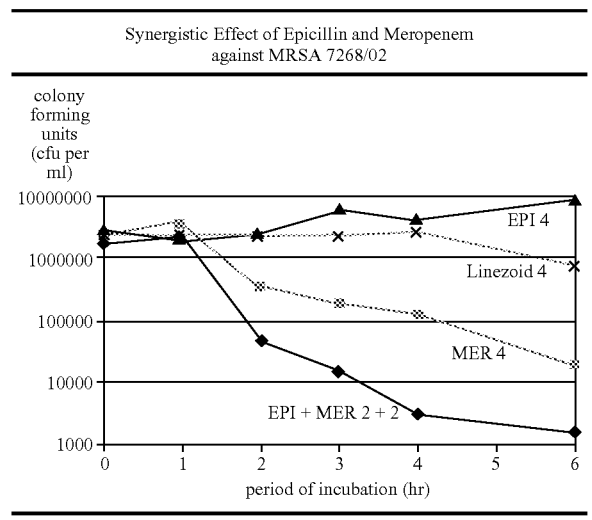

Using the same bacterium and concentrations, the combination epicillin/meropenem gave a reduction in cfu's by 99.7% as compared to 42.5% for piperacillin/meropenem. Similarly, with *Staph. aureus* Innsbruck at 4+4 µg/ml, reduction of cfu's after 6 hrs of incubation at 37° C. by epicillin/meropenem was 100% as compared to a marginal 10% reduction achieved by piperacillin/meropenem (Table 3). The bactericidal activity of epicillin/meropenem was also superior to ampicillin/meropenem and amoxicillin/meropenem. Similarly, other epicillin/carbapenem combinations also had the very fast bactericidal action.

In short, the combination of epicillin with a carbapenem is more active, more bactericidal and faster than corresponding preparations of prior art in eradicating MRSA.

TABLE 3

Bactericidal effect of Penicillins/ Meropenem against Staph. Innsbruck

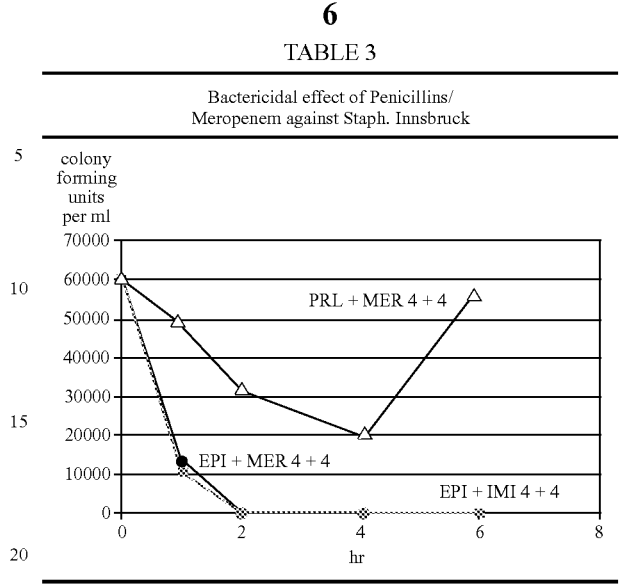

The high bactericidity of this combination is in sharp contrast to the current antibiotics used against MRSA, i.e. linezolide and vancomycin, both having only bacteriostatic activity (Chemotherapie Journal. 2002, 11, 113-6; Antimicrob. Ag. Chemother. (2005), 49, 2735).

The high synergistic activity of the combination epicillin/meropenem is also observed in the plate test with the following diameters of inhibition zones:

|  |  | MRSA 7268/02 | Staph. Innsbruck |
|---|---|---|---|
| Epicillin (alone) | 30 µg | 14 mm | 10 mm |
| Meropenem (alone) | 10 µg | 13 mm | 14 mm |
| Epi and Mero | 30 + 10 µg | 23 mm | 20 mm |
| Vancomycin | 30 µg | 19 mm | 20 mm |

Unlike the inhibition zones caused by the single substances epicillin or meropenem, and unlike all investigated single β-lactams, those generated by the combination of epicillin and meropenem remained clear after additional incubation (40 hr) at 37° C., confirming the above-mentioned strong bactericidal effect. This effect is also observable with other epicillin/carbapenem combinations. Therefore the use of a composition of epicillin and a carbapenem is strongly preferred.

The high bactericidity of this combination is also in sharp contrast to that of e.g. oxacillin/meropenem. No synergism of the latter composition was observed in the plate test.

|  |  | MRSA 7268/02 | Staph. Innsbruck |
|---|---|---|---|
| Oxacillin (alone) | 30 µg | 0 mm | 0 mm |
| Meropenem (alone) | 10 µg | 13 mm | 13 mm |
| Oxacillin and Mero | 30 + 10 µg | 13 mm | 13 mm |

The high and fast bactericidal activity of a combination of two β-lactam compounds, e.g. epicillin and meropenem against MRSA is surprising. It has been stated by prior art, that all β-lactams should be reported "resistant" to methicillin (or oxacillin) (W. Cullmann in "Antibiotics and Chemotherapy" Vol. 47 (Oral Cephalosporins), p. 79 (1995). This citation constitutes a prejudice of prior art against the present invention.

The use of carbapenems and epicillin to eradicate MRSA or MRSE is not known by prior art. No references were available from Sci-Finder Scholar (Am. Chem. Society) using both key words "epicillin and mrsa", whereas 9082 references were available with the (single) key word "mrsa".

An objective of the present invention is to provide a novel pharmaceutical composition of a carbapenem antibiotic and epicillin which proves to have a very broad antibacterial spectrum including MRSA and MRSE. The above mentioned synergism with epicillin is also inherent to orally active carbapenems.

Epicillin was widely used in the 1970s and 1980s as orally and parenterally active antibiotic. A report of clinical experience is given e.g. in N. Z. med. J. 75, 77 (1972). The carbapenems are either commercial products or are prepared by a method described in EP 1 100 800 or are described elsewhere, e.g. in Heterocycles, 54, 497 (2001); Drugs 61, 553 (2001); Current Opinion in Anti-Infective Investigational Drugs 2, 133 (2000);

As already mentioned, the selection of carbapenems in the preparation of synergistic mixtures is not very critical. In fact all 18 carbapenems so far investigated showed a pronounced synergism against MRSA when combined with epicillin. On the other hand, the selection of partner antibiotics is more crucial. In contrast to teaching of prior art, only epicillin can provide sufficient bactericidal activity to eradicate MRSA which have a high resistance level in the synergistic action with carbapenems.

For oral use, prodrug esters or prodrug amide derivatives of epicillin can also be applied to prepare synergistic preparations. Such prodrugs are known in the art and described e.g. in Advances in Drug Res. 17, 197 (1988) or in Curr. Med. Chem.—Anti-Infective Agents 2002, 1, 1. Examples of such prodrug esters derived of similar antibiotics are pivampicillin, bacampicillin and pivcefalexin. An example for prodrug amide derivatives is hetacillin.

Examples of useful conventional carbapenems in the preparation of synergistic mixtures are the carbapenems described in EP 1 100 800, imipenem, imipenem/cilastatin, meropenem, panipenem, panipenem/betamipron, ertapenem, biapenem, doripenem, saftrinem, lenapenem, tebipenem, tomopenem S-4661, SM 216601, GV 129606, ZD-4433, ER-35786, R-83201, R 95867, DU-6681, BO-2502A, BO-3482, DK-35C, DA-1131, S-4661, L-646591, L-786, 392, L-695,256, L-786,392, L-084, L-036, GV104326, GV-118819, GV 143253, MK-0826, J-110,441, J-111225, FR-21818, DX-8739, CS-023, ME-1036, CP 5068, OCA-983, CL 188624, CL-190294, T-5575, PZ-601.

Equivalently, for oral use, hydrolysable prodrug esters, also known in the field of carbapenems (Antimicrob. Agents, Chemother. 1998, 42, 1527; Heterocycles 54, 497 (2001), Curr. Med. Chem.—Anti-infective Agents 2002, 1, 1), can be used to prepare synergistic mixtures. Examples of prodrug carbapenems are CS-834, L-084, GV118819, DZ-2640, CL191121.

The ratio of carbapenem to epiciilin can vary within a large scope. Useful ratios are 1:10 to 10:1. Preferred ratios are 1:4 to 4:1. Strongly preferred ratios are 1:1 to 1:3

The above-mentioned combination of epicillin and a carbapenem can be supplemented with a variety of other biologically active ingredients. Examples are dehydropeptidase inhibitors such as betamipron or cilastatin, which is used currently to protect carbapenems such as imipenem.

The fast and progressive reduction of colony forming units makes the inventive combinations the method of choice as initial therapy for confirmed or suspected MRSA and MRSE infections.

A major drawback with infectious diseases is emergence of life threatening sepsis, a severe illness from a bloodstream infection. It is estimated that bacterial sepsis kills more than 200 000 people per year in the US (www.nursing-home-abuse-resource.com). Sepsis is also common with MRSA. To avoid such threat, bacterial units can be reduced by the initial bactericidal therapy according to the invention. Then a secondary therapy with an antibiotic, e.g. an antibiotic other than a β-lactam, can follow up to eradicate the largely diminished number of bacteria. Therefore, the inventive combination may be further supplemented with antibiotics. Examples for such supplements are sulfonamides, e.g. sulfathiazole/trimethoprim, tetracyclines, e.g. aureomycin or doxycycline, aminoglycosides, e.g. clindamycin, glycopeptides, e.g. teicoplanin, vancomycin, quinolones, e.g. ciprofloxacin, moxifloxacin, gatifloxacin or rifamycins e.g. rifampin, macrolides, e.g. erythromycin or other bacteriostatic agents, e.g. linezolid.

A selection of pharmaceutical preparations according to the invention showed also high antibacterial activity against bacteria different from staphylococci: In the disc susceptibility test, simultaneous application of 30 micrograms of epicillin and 10 micrograms of carbapenem gave the following inhibition diameters: *E. coli* (27-40 mm), *E. cloacae* (23-27 mm), *Sr. pneumoniae* (31-44 mm), *Enterococcus faecalis* (21-40 mm) and *Ps. aeruginosa* (13-26 mm). These data correspond to those of a clinically useful injectable carbapenem used as a single substance as described in Journ. Antimicrob. Chemotherapy 24, (1989), Suppl. A, 253.

The new pharmaceutical preparations are valuable bactericides to be used in human and veterinary medicine. Due to their large antibacterial spectrum they can also be used as medicaments for treating suspected or confirmed infections that are caused by other than the above-mentioned Gram-positive and Gram-negative bacteria, i.e. by MRSA, MRSE, *Moraxella catharrhalis, Haemophilus influenzae, Klebsiella pneumoniae, Bacillus subtilis, Salmonella typhosa, Enterobacter cloacae, Citrobacter, Pseudomonas aeruginosa, Bacteriumproteus* and anaerobic bacteria.

A major field of antimicrobial therapy using carbapenems as single substances is sinusitis, an inflammation of the respiratory tract. Bacterial sinusitis is caused predominantly by *streptococcus pneumomiae, moraxella catharrhalis, haemophilus influenzae*, some anaerobic bacteria and penicillin sensitive and penicillin resistant (β-lactamase producing) *staphylococcus aureus* and MRSA, often emerging also in mixed infections (Journal of laryngology and otology (2005), 119(4), 251). Carbapenems alone can eradicate efficiently all of these bacteria except MRSA. The combination of a carbapenem/epicillin composition closes the gap arising from the resistance of MRSA. Therefore, the inventive combination is especially useful to cure bacterial sinusitis. Furthermore, other infectious diseases, e.g. urinary tract infections or wounds, confirmed or assumed to be caused by MRSA or MRSE, can be cured by application of the pharmaceutical composition according to the invention.

The new bactericidal MRSA active pharmaceutical compositions according to the invention are valuable remedies which are active against most Gram-positive and Gram-negative pathogens including also most penicillin- and cephalosporin resistant and anaerobic bacteria. Due to their very broad antibacterial spectrum, they are valuable medicaments for use, e.g. in intensive care units. On the other hand, since epicillin is an orally active drug, its combination with orally active carbapenems provides also valuable remedies for rapid oral treatment of community-acquired infections.

The pharmaceutical compositions according to the invention can contain the free acid and in particular the alkaline and earth metal salts or the zwitterionic species of their components. They are useful bactericides and can be employed to remove pathogens from dental and medical equipment for removing microorganisms and for therapeutic use in humans and animals. For the latter purposes, pharmaceutically acceptable salts of their active components can be used, as are known per se and are used in the administration of penicillins and cephalosporins. These salts can be used together with pharmaceutically acceptable liquid and solid excipients to form suitable dose unit forms such as pills, tablets, capsules, suppositories, syrups, elixirs and the like, which can be prepared by processes which are known per se.

The new pharmaceutical preparations can furthermore be used as additives for animal feeds, for preserving foodstuffs or feeds and as desinfectants. For example, they can be used in aqueous preparations in concentrations in the range 0.1 to 100 parts of antibiotic/million parts of solution for destroying and inhibiting the growth of harmful bacteria on medical equipment and as bactericides in industrial applications, for example in water-based paints and in soft water for paper mills, for inhibiting the growth of harmful bacteria.

The new pharmaceutical composition according to the invention may be used alone or together with other active components in any of a large number of pharmaceutical preparations. These preparations can be used in capsule form or as tablets, powders or liquid solutions or as suspensions or elixirs. They can be administered orally, intraperitoneally, intravenously or intramuscularly.

The preparation is preferably administered in a form which is suitable for absorption through the gastrointestinal tract. Tablets and capsules for oral administration may be in dose unit form and can contain customary medicament excipients, such as binders, for example syrup, gum arabic, gelatin, sorbitol or polyvinylpyrrolidone, fillers, for example lactose, sugar, maize starch, calcium phosphate, sorbitol or glycine, lubricants, for example magnesium stearate, talc, polyethylene glycol or silica, disintegrants for example potato starch, or acceptable wetting agents such as sodium lauryl sulfate. The tablets may be coated by processes which are known per se. Oral liquid preparations can be in the form of aqueous or oily suspensions, solutions, emulsions, syrups, elixirs and the like or can exist as dry products, for example for reconstitution before using water or other suitable excipients. Liquid preparations of this type can contain additives which are known per se, such as suspending agents, for example sorbitol syrup, methylcellulose, glucose/sugar syrup, gelatin, hydroxyethylcellulose, carboxymethylcellulose, aluminum stearate gel, or hydrogenated edible oils, for example almond oil, fractionated coconut oil, oily esters, propylene glycol or ethyl alcohol, preservatives, for example methyl or propyl p-hydroxybenzoate or sorbic acid. Suppositories contain suppository bases which are known per se, for example cocoa butter or other glycerides.

The preparations for injection can be in dose unit form in ampoules or in containers containing several doses along with an added preservative. The preparations can be in the form of suspensions, solutions or emulsions in oily or aqueous excipients, and they may contain formulation agents such as suspending agents, stabilizers and/or dispersants. Alternatively, the active component may be in powder form for reconstitution before using a suitable excipient, for example sterile, pyrogen-free water.

The preparations can also be in suitable form for absorption through the mucous membranes of the nose and of the throat or of the bronchial tissue, and can be in the form of powders or liquid sprays or inhalants, sucking sweets, as throat paints, etc.

For eye and ear medications, the preparations can be used in the form of individual capsules in liquid or semi-solid form or they can be used as drops, etc. Topical applications can exist or be formulated in hydrophobic vehicles as ointments, creams, lotions, paints, powders, etc.

The two active components, i.e. the carbapenem and epicillin may also be administered separately. For example, a carbapenem can be administered by the intravenous route and epicillin by the oral route. Conveniently however, the two active agents will be administered by the same route, e.g. the intravenous route or the oral route.

The composition according to the invention can contain, in addition to the excipient, other components such as stabilizers, binders, antioxidants, preservatives, lubricants, suspending agents, viscosity control agents or flavours or the like.

The composition according to the invention may also contain, in addition to the excipient, enzyme inhibitors, e.g. betamipron or cilastatin (Merck Index, 11th ed. 2275) to increase the therapeutic effect.

For veterinary medicine, the composition can be formulated, for example, as an intramammary preparation in either long-acting or rapid-release vehicles. The dose to be administered is highly dependent on the state of the subject to be treated and the weight of the host, and on the method and frequency of administration. In general, a daily oral dose contains about 10 to 200 mg of active component/kg of body weight of the subject in case of one or more administrations per day. A preferred daily dose for adult humans is in the range of 20 to 120 mg of active component/kg of body weight.

The preparation according to the invention can be administered in various unit dose forms, for example in solid or liquid dose forms which can be taken orally. The preparation can contain 0.1 to 99% of active material per unit dose, either in solid or in liquid form. The preferred range is about 10 to 60%. The preparations generally contain 15 to about 1500 mg of active component but it is generally preferred to use a dose amount in the range of 250 to 1000 mg. In the case of parenteral administration, the unit dose is normally the pure compound in a sterile water solution or in the form of a soluble powder, which may be dissolved.

The examples below illustrate the antibacterial activities, in comparison with pharmaceutical compositions described by prior art. In addition, preparations and methods of treatment according to the invention are exemplified.

EXAMPLE 1

Antibacterial Activity Determined by Agar Diffusion Method

Inhibition zone diameters were determined on Difco Nutrient Agar (10 ml) in sterile dishes (8.5 cm) using ca. $10^6$-$10^7$ colony forming units. 0.2 ml of a bacterial suspension (overnight culture in Difco Nutrient Broth) was mixed at 52° C. with the sterile liquid agar. It solidified at room temperature. Sterile filter disks (6 mm) were placed on the agar surface. Appropriate volumes of a 0.2% aqueous solutions of antibiotics were transferred to the disks by a precision syringe. Alternatively, commercial impregnated disks (Oxoid) were used.

The inhibition zone diameter was measured after 20 hrs at 37° C. For determination of bactericidal activity, incubation at 37° C. was continued for additional 40 hrs. A clear inhibition zone after additional incubation indicated bactericidity (B).

| Test strain MRSA 7268/02 | | |
|---|---|---|
| Epicillin (30 μg) 14 | Meropenem (10 μg) 13 | Epicillin + Meropenem (30 + 10 μg) 23 (B) |
| Epicillin (30 μg) 14 | Imipenem (10 μg) 14 | Epicillin + Imipenem (30 + 10 μg) 24 (B) |
| Epicillin (30 μg) 12 | R 83201 (10 μg) 9 | Epicillin + R 83201 (30 + 10 μg) 20 (B) |
| Epicillin (30 μg) 12 | Ertapenem (10 μg) 0 | Epicillin + Ertapenem (30 + 10 μg) 16 (B) |
| Epicillin (30 μg) 14 | GH 478 (10 μg) 0 | Epicillin + GH 478 (30 + 10 μg) 23 (B) |
| Epicillin (30 μg) 12 | GH 570 (10 μg) 0 | Epicillin + GH 570 (30 + 10 μg) 19 (B) |
| Epicillin (30 μg) 12 | GH 519 (10 μg) 0 | Epicillin + GH 519 (30 + 10 μg) 16 (B) |
| Cefaclor (30 μg) 11 | GH 478 (10 μg) 0 | Cefaclor + GH 478 (30 + 10 μg) 19 |
| Amoxicillin (30 μg) 0 | GH 478 (10 μg) 0 | Amoxicillin + GH 478 (30 + 10 μg) 17 |
| Amoxyclav (30 μg) 13 | GH 478 (10 μg) 0 | Amoxyclav + GH 478 (30 + 10 μg) 17 |
| Ampicillin (30 μg) 12 | GH 478 (10 μg) 0 | Ampicillin + GH 478 (30 + 10 μg) 21 |
| Cloxacillin (30 μg) 0 | GH 478 (10 μg) 0 | Cloxacillin + GH 478 (30 + 10 μg) 0 |
| Dicloxacillin (30 μg) 0 | GH 478 (10 μg) 0 | Dicloxacillin + GH 478 (30 + 10 μg) 0 |
| Cefazolin (30 μg) 0 | GH 478 (10 μg) 0 | Cefazolin + GH 478 (30 + 10 μg) 11 |
| Cephalothin (30 μg) 0 | GH 478 (10 μg) 0 | Cephalothin + GH 478 (30 + 10 μg) 9 |
| Cefoxitin (30 μg) 0 | GH 478 (10 μg) 0 | Cefoxitin + GH 478 (30 + 10 μg) 0 |
| Cefuroxim (30 μg) 0 | GH 478 (10 μg) 0 | Cefuroxim + GH 478 (30 + 10 μg) 14 |
| Cefdinir (30 μg) 0 | GH 478 (10 μg) 0 | Cefdinir + GH 478 (30 + 10 μg) 0 |
| Cefotaxime (30 μg) 0 | GH 478 (10 μg) 0 | Cefotaxime + GH 478 (30 + 10 μg) 10 |
| Oxacillin (30 μg) 0 | GH 478 (10 μg) 0 | Oxacillin + GH 478 (30 + 10 μg) 0 |
| Ceftriaxon (30 μg) 0 | GH 478 (10 μg) 0 | Ceftriaxon + GH 478 (30 + 10 μg) 10 |
| Carbenicillin (30 μg) 0 | GH 478 (10 μg) 10 | Carbenicillin + GH 478 (30 + 10 μg) 15 |
| Cefazolin (30 μg) 0 | GH 478 (10 μg) 0 | Cefazolin + GH 478 (30 + 10 μg) 13 |
| Cefoperazone (30 μg) 9 | GH 478 (10 μg) 0 | Cefoperazone + GH 478 (30 + 10 μg) 10 |
| Cefotiam (30 μg) 10 | GH 478 (10 μg) 0 | Cefotiam + GH 478 (30 + 10 μg) 14 |
| Cefotiam (30 μg) 0 | Imipenem (10 μg) 8 | Cefotiam + Imipenem (30 + 10 μg) 12 |
| Piperacillin (30 μg) 0 | Imipenem (10 μg) 8 | Piperacillin + Imipenem (30 + 10 μg) 13 |
| Cefsudolin (30 μg) 0 | GH 478 (10 μg) 0 | Cefsudolin + GH 478 (30 + 10 μg) 0 |
| Vancomycin (30 μg) 19 | | |

| Test strain: Staph. Innsbruck | Diameter of inhibition zone (mm) | |
|---|---|---|
| Epicillin (30 μg) 10 | Meropenem (10 μg) 14 | Epicillin + Meropenem (30 + 10 μg) 20 (B) |
| Epicillin (30 μg) 10 | Imipenem (10 μg) 14 | Epicillin + Imipenem (30 + 10 μg) 22 (B) |
| Epicillin (30 μg) 14 | GH 478 (10 μg) 0 | Epicillin + GH 478 (30 + 10 μg) 19 (B) |
| Epicillin (30 μg) 12 | R 83201 (10 μg) 11 | Epicillin + R 83201 (30 + 10 μg) 20 (B) |
| Epicillin (30 μg) 12 | Ertapenem (10 μg) 0 | Epicillin + Ertapenem (30 + 10 μg) 16 (B) |
| Epicillin (30 μg) 12 | GH 570 (10 μg) 0 | Epicillin + GH 570 (30 + 10 μg) 17 (B) |
| Epicillin (30 μg) 12 | GH 519 (10 μg) 0 | Epicillin + GH 519 (30 + 10 μg) 16 (B) |
| Amoxicillin (30 μg) 10 | GH 478 (10 μg) 0 | Amoxicillin + GH 478 (30 + 10 μg) 17 |

-continued

| | | |
|---|---|---|
| Amoxyclav (30 μg) 13 | GH 478 (10 μg) 0 | Amoxyclav + GH 478 (30 + 10 μg) 17 |
| Ampicillin (30 μg) 12 | GH 478 (10 μg) 0 | Ampicillin + GH 478 (30 + 10 μg) 17 |
| Penicillin G (30 μg) 12 | GH 478 (10 μg) 0 | Penicillin G + GH 478 (30 + 10 μg) 14 |
| Cefixim (30 μg) 0 | GH 478 (10 μg) 0 | Cefixim + GH 478 (30 + 10 μg) 9 |
| Cefazolin (30 μg) 0 | GH 478 (10 μg) 0 | Cefazolin + GH 478 (30 + 10 μg) 11 |
| Cefoxitin (30 μg) 11 | GH 478 (10 μg) 0 | Cefoxitin + GH 478 (30 + 10 μg) 11 |
| Cefotaxime (30 μg) 0 | GH 478 (10 μg) 0 | Cefotaxime + GH 478 (30 + 10 μg) 9 |
| Piperacillin (30 μg) 0 | GH 478 (10 μg) 0 | Piperacillin + GH 478 (30 + 10 μg) 11 |
| Oxacillin (30 μg) 0 | GH 478 (10 μg) 0 | Oxacillin + GH 478 (30 + 10 μg) 0 |
| Cloxacillin (30 μg) 0 | GH 478 (10 μg) 0 | Cloxacillin + GH 478 (30 + 10 μg) 11 |
| Diloxacillin (30 μg) 0 | GH 478 (10 μg) 0 | Dicloxacillin + GH 478 (30 + 10 μg) 0 |
| Ceftriaxon (30 μg) 0 | GH 478 (10 μg) 0 | Ceftriaxon + GH 478 (30 + 10 μg) 0 |
| Moxalactam (30 μg) 8 | GH 478 (10 μg) 0 | Moxalactam + GH 478 (30 + 10 μg) 10 |
| Ceftriaxon (30 μg) 0 | GH 478 (10 μg) 0 | Ceftriaxon + GH 478 (30 + 10 μg) 0 |
| Cefotiam (30 μg) 0 | Imipenem (10 μg) 8 | Cefotiam + Imipenem (30 + 10 μg) 15 |
| Piperacillin (30 μg) 0 | Imipenem (10 μg) 8 | Piperacillin + Imipenem (30 + 10 μg) 13 |
| Penicillin G (30 μg) 0 | GH 478 (10 μg) 0 | Penicillin G + GH 478 (30 + 10 μg) 14 |
| Methicillin (30 μg) 0 | GH 478 (10 μg) 0 | Methicillin + GH 478 (30 + 10 μg) 0 |
| Cefsudolin (30 μg) 0 | GH 478 (10 μg) 0 | Cefsudolin + GH 478 (30 + 10 μg) 10 |
| Vancomycin (30 μg) 20 | | |

GH 478: Potassium (1R,5S,6S)-6-[(R)-1-hydroxyethyl]-2-methoxymethylthio-1-methylcarbapen-2-em-3-carboxylate
GH 570: (1R,5S,6S)-2-[(2-Aminoethyl)oxy]metlhylthio-6-[(R)-1-hydroxyethyl]-1-methylcarbapen-2-em-3-carboxylic acid
GH 519: Potassium (1R,5S,6S)-2-[(N-acetylamino)methylthio]-6-[(R)-1-hydroxyethyl]-1-methyl-carbapenen-2-em-3-carboxylate

EXAMPLE 2

Minimal Inhibitory Concentrations

Minimal inhibitory concentrations were determined using Difco Nutrient Agar. Appropriate volumes of 0.1% aqueous solutions of antibiotics were added into sterile dishes (8.5 cm) in twofold dilutions and mixed with 10 ml of sterile liquid agar of 50° C. The solid agar was inoculated with 3 μl of an 0.5 McFarland bacterial solution in Difco Nutrient Broth, corresponding to approx. $10^5$ colony forming units. Bacterial growth was recorded after 20 hrs of incubation at 37° C.

| | Minimal Inhibitory concentration (μg/ml) | |
|---|---|---|
| | MRSA 7268/02 | Staph. Innsbruck |
| Epicillin | 32 | 32 |
| Amoxycillin | 32 | 64 |
| Meropenem | 16 | 32 |
| Cefoxitin | | 32 |
| Cefotiam/Imipenem | | 16 + 16 |
| Piperacillin/Meropenem | 8 + 8 | 16 + 16 |
| Piperacillin/Imipenem | 16 + 16 | 16 + 16 |
| Epicillin/Meropenem | 2 + 2 | 4 + 4 |
| Epicillin/Imipenem | 1 + 1 | 4 + 4 |

EXAMPLE 3

In Vivo Activity

In vivo activity was determined by a mouse septicaemia test using immunocompetent animals of 30 g weight (6 animals per group). Infection was performed with MRSA München 12797 at a concentration of approx. $2 \times 10^9$ cfu/mouse by the i.v. route (lethal dose). Therapy was performed at daily doses from 5+5 to 75+75 mg/kg by s. c. route (equivalent amounts at time 1 hr and 4 hr after infection). The animals were observed for 10 days post treatment.

$ED_{90}$ meropenem>75+75 mg/kg
$ED_{90}$ meropenem/epicillin≦5+5 mg/kg

EXAMPLE 4

Production of Pharmaceutical Preparations

| Tablet (for oral application) | |
|---|---|
| Potassium (4R,5S,6S)-6-(1'R)-hydroxyethyl)-3-methoxymethylthio-4-methyl-7-oxo-1-azabicyclo[3.2.0]hept-2-ene-2-carboxylate | 250 mg |

-continued

| Tablet (for oral application) | |
|---|---|
| Epicillin | 500 mg |
| Corn starch | 6 mg |
| Magnesium stearate | 20 mg |
| Sodium hydrogen carbonate | 135 mg |
| Dicalcium phosphate | 60 mg |
| Lactose | 229 mg |

The active constituent is mixed with the dicalcium phosphate, lactose and about half of the corn starch and coarse-sieved. It is dried in high vacuum and again sieved through sieves having mesh widths of 1.00 mm (No. 16 screens). The rest of the corn starch and the magnesium stearate is added and the mixture is pressed to give tablets which each weight 1200 mg and have a diameter of about 1.27 cm (0.5 in.).

Parenteral Solution

| Ampoule | |
|---|---|
| Meropenem | 250 mg |
| Epicillin | 250 mg |
| Sodium hydrogen carbonate | 135 mg |
| Sterile water (is added from a separate ampoule using a syringe immediately before use) | 4 ml |

| Ophtalmic solution | |
|---|---|
| Meropenem | 50 mg |
| Epicillin | 50 mg |
| Sodium hydrogen carbonate | 27 mg |
| Hydroxypropylmethylcellulose | 5 mg |
| Sterile water (is added from a separate ampoule using a syringe immediately before use) | 2 ml |

| Otic solution | |
|---|---|
| Meropenem | 50 mg |
| Epicillin | 50 mg |
| Sodium hydrogen carbonate | 27 mg |
| Benzalkonium chloride | 0.1 mg |
| Sterile water (is added from a separate ampoule using a syringe immediately before use) | 2 ml |

| Topical cream or ointment | |
|---|---|
| Meropenem | 50 mg |
| Epicillin | 50 mg |
| Polyethylene glycol 4000 | 400 mg |
| Polyethylene glycol 400 | 1.0 g |

The active component in the above preparations can be mixed alone or together with other biologically active components, for example with other antibacterial agents such as vancomycin or linezolide or with other therapeutic agents, such as probenicid.

It is understood that the specification and examples are illustrative but not limitative of the present invention and that other embodiments within the spirit and scope of the invention will suggest themselves to those skilled in the art.

The invention claimed is:

1. A pharmaceutical composition comprising a carbapenem antibiotic and epicillin, or salts, prodrug ester or prodrug amide derivatives thereof, wherein the carbapenem antibiotic is selected from the group consisting of imipenem, meropenem, panipenem, ertapenem, biapenem, doripenem, saftrinem, lenapenem, tebipenem, tomopenem, SM-216601, ER-35786, R-83201, R 95867, DU-6681, BO-2502A, BO-3482, DK-35C, DA-1131, L-646591, L-084, DZ-2640, CS-834, MK-826, J-110441, J-111225, FR-21818, DX-8739 CL 188624, CL-190294, CL-191121, OCA-983, (4R,5S,6S) 1-azabicyclo[3.2.0]hept-2-ene-2-carboxylic acid, 6-[(R)-1-hydroxyethyl]-3-[methoxymethyl]thio-4-methyl-7-oxo; (4R,5S,6S) 1-azabicyclo[3.2.0]hept-2-ene-2-carboxylic acid, 3-[2-(aminoethyl)oxy]methyl]thio-6-[(R)-I-hydroxyethyl]-4-methyl-7-oxo; and (4R,5S,6S) 1-azabicyclo[3.2.0]hept-2-ene-2-carboxylic acid, 3-[(N-acetylamino)methyl]thio-6-[(R)-1-hydroxyethyl]-4-methyl-7-oxo.

2. The pharmaceutical composition according to claim 1, wherein the carbapenem antibiotic is selected from the group consisting of imipenem, meropenem, panipenem, ertapenem, biapenem, doripenem, lenapenem, tebipenem and tomopenem.

3. The pharmaceutical composition according to claim 2, wherein the carbapenem antibiotic is selected from the group consisting of imipenem, meropenem and ertapenem.

4. The pharmaceutical composition according to claim 1, comprising effective amounts of a carbapenem antibiotic and epicillin and a pharmaceutically acceptable carrier or diluent.

5. The pharmaceutical composition of claim 1, wherein the pharmaceutical composition comprises imipenem and epicillin, or a salt, prodrug ester or prodrug amide derivative thereof.

6. The pharmaceutical composition of claim 1, wherein the pharmaceutical composition comprises meropenem and epicillin, or a salt, prodrug ester or prodrug amide derivative thereof.

7. The pharmaceutical composition of claim 1, wherein the carbapenem antibiotic is:
   (4R,5S,6S) 1-azabicyclo[3.2.0]hept-2-ene-2-carboxylic acid, 6-[(R)-1-hydroxyethyl]-3-[methoxymethyl]thio-4-methyl-7-oxo;
   (4R,5S,6S) 1-azabicyclo[3.2.0]hept-2-ene-2-carboxylic acid,3-[[2-(aminoethyl)oxy]methyl]thio-6-[(R)-1-hydroxyethyl]-4-methyl-7-oxo; or
   (4R,5S,6S) 1-azabicyclo[3.2.0]hept-2-ene-2-carboxylic acid, 3-[(N-acetylamino)methyl]thio-6-[(R)-1-hydroxyethyl]-4-methyl-7-oxo;
   or a salt, prodrug ester or prodrug amide derivative thereof.

8. A process for preparing the composition according to claim 1, which comprises incorporating antibacterially effective amounts of a carbapenem antibiotic and epicillin or salts, prodrug ester or prodrug amide derivatives thereof into a pharmaceutically acceptable carrier or diluent.

9. A method of inhibiting confirmed or suspected MRSA or MRSE in a patient in need thereof, which comprises administering to said patient effective amounts of a carbapenem antibiotic and epicillin according to claim 1 and a pharmaceutically acceptable carrier or diluent.

10. A method of inhibiting confirmed or suspected MRSA or MRSE in a patient in need thereof, which comprises separate administration to the patient of effective amounts of a carbapenem antibiotic and epicillin according to claim 1 and a pharmaceutically acceptable carrier or diluent.

* * * * *